US012108900B1

(12) United States Patent
Marcus et al.

(10) Patent No.: US 12,108,900 B1
(45) Date of Patent: Oct. 8, 2024

(54) AUTOMATED SLEEP ASSISTANT

(71) Applicant: Amazon Technologies, Inc., Seattle, WA (US)

(72) Inventors: Beth A. Marcus, Bedford, MA (US); Margaret Jean Williams George, Cambridge, MA (US)

(73) Assignee: Amazon Technologies, Inc., Seattle, WA (US)

( * ) Notice: Subject to any disclaimer, the term of this patent is extended or adjusted under 35 U.S.C. 154(b) by 226 days.

(21) Appl. No.: 17/544,473

(22) Filed: Dec. 7, 2021

(51) Int. Cl.
*A47G 9/10* (2006.01)
*A61B 5/00* (2006.01)
(Continued)

(52) U.S. Cl.
CPC ......... *A47G 9/1045* (2013.01); *A47G 9/1027* (2013.01); *A47G 9/1036* (2013.01);
(Continued)

(58) Field of Classification Search
CPC .. A47G 9/1045; A47G 9/1027; A47G 9/1036; A47G 2200/146; A47G 2200/205; A47G 9/1081; A47G 2009/003; A47G 2009/006; A47G 9/10; A47G 2200/143; A47G 2200/20; A47G 2009/1018; A61B 5/1116; A61B 5/113; A61B 5/4818; A61B 5/6843; A61B 5/7455; A61B 5/4806; A61B 5/024; A61B 5/0816; A61B 5/4812; G06N 20/00; A61F 5/56
See application file for complete search history.

(56) References Cited

U.S. PATENT DOCUMENTS

2007/0061976 A1* 3/2007 Bazargani ............ A47G 9/1027 5/644
2016/0270948 A1* 9/2016 Hariri .................. A61H 9/0078

FOREIGN PATENT DOCUMENTS

CA 3030904 A1 * 1/2010 ............. G16H 50/30
CN 111281642 * 3/2020 ........... A61B 5/7203
(Continued)

OTHER PUBLICATIONS

"Algorithm." Cambridge Dictionary, Feb. 12, 2018, https://dictionary.cambridge.org/US/dictionary/english/algorithm (Year: 2018).*

*Primary Examiner* — Justin C Mikowski
*Assistant Examiner* — Madison Emanski
(74) *Attorney, Agent, or Firm* — Eversheds Sutherland (US) LLP

(57) ABSTRACT

Systems, devices, and methods are provided for an automated sleep assistant. An automated sleep assistant may comprise an audio input device for capturing sounds and utterances made by a user while sleeping. Audio data may be collected and analyzed to identify sleep patterns indicative of an adverse sleep-related condition such as Obstructive Sleep Apnea (OSA). A pillow comprising a plurality of regions with one or more sensors, one or more inflatable air bladders, and one or more haptic feedback devices may be utilized. A base unit device physically connected to the pillow may determine one or more external forces that mitigate the adverse sleep-related condition and cause the pillow to apply the one or more external forces to the user, for example, by using a pump to inflate an air bladder to help the user's head lift or tip to a specific angle that opens his or her airway.

19 Claims, 7 Drawing Sheets

(51) Int. Cl.
  *A61B 5/11*    (2006.01)
  *A61B 5/113*   (2006.01)
  *A61F 5/56*    (2006.01)
  *G06N 20/00*   (2019.01)

(52) U.S. Cl.
  CPC ............ *A61B 5/1116* (2013.01); *A61B 5/113* (2013.01); *A61B 5/4818* (2013.01); *A61B 5/6843* (2013.01); *A61B 5/7455* (2013.01); *A61F 5/56* (2013.01); *G06N 20/00* (2019.01); *A47G 2200/146* (2013.01); *A47G 2200/205* (2013.01)

(56)          References Cited

FOREIGN PATENT DOCUMENTS

| JP | 2006136515 A  | * | 6/2006  | ............ A61M 21/02 |
| KR | 101762116 B1  | * | 8/2017  | ............ A47G 9/1027 |
| KR | 10180442 B1   | * | 10/2017 | ............... A61F 5/56 |
| KR | 102052099 B1  | * | 12/2019 | ............ A47G 9/1027 |
| KR | 102137927 B1  | * | 3/2020  | ............ A61H 1/0296 |

\* cited by examiner

AUTOMATED SLEEP ASSISTANT

BACKGROUND

According to the World Sleep Society, globally 3.5 billion people suffer from sleep disorders. Obstructive Sleep Apnea (OSA) is a common type of sleep-related breathing disorder caused by weak muscles in the tongue and around the neck area. OSA may be characterized by recurrent episodes of complete or partial obstruction of the upper airway leading to reduced or absent breathing during sleep. As a consequence, there are several possible consequences of OSA, including snoring, variability of blood pressure and cardiovascular morbidities.

There are various shortcomings to existing solutions used to treat OSA. Positive airway pressure machines such as continuous positive airway pressure (CPAP) machines and implantable devices are used as a common type of therapeutic intervention that provides a positive airway pressure. However, these solutions are typically expensive, inconvenient, and/or expensive. A CPAP machine requires the user to wear a mask that covers the mouth and nose, which users may find uncomfortable and obtrusive. However, some users do not realize consistent benefits of CPAP machines. Another option is to use an implantable device placed within the neck that is used during sleep to help stimulate the muscles that open the user's airway. However, implants require a surgical procedure to be performed, which carries additional risks and may not be suitable for all users.

Therefore it would be desirable to provide a new and non-invasive systems and techniques for addressing sleep disorders such as OSA, muscular sleep disturbance, snoring or other sleep disruption.

Figure 1:
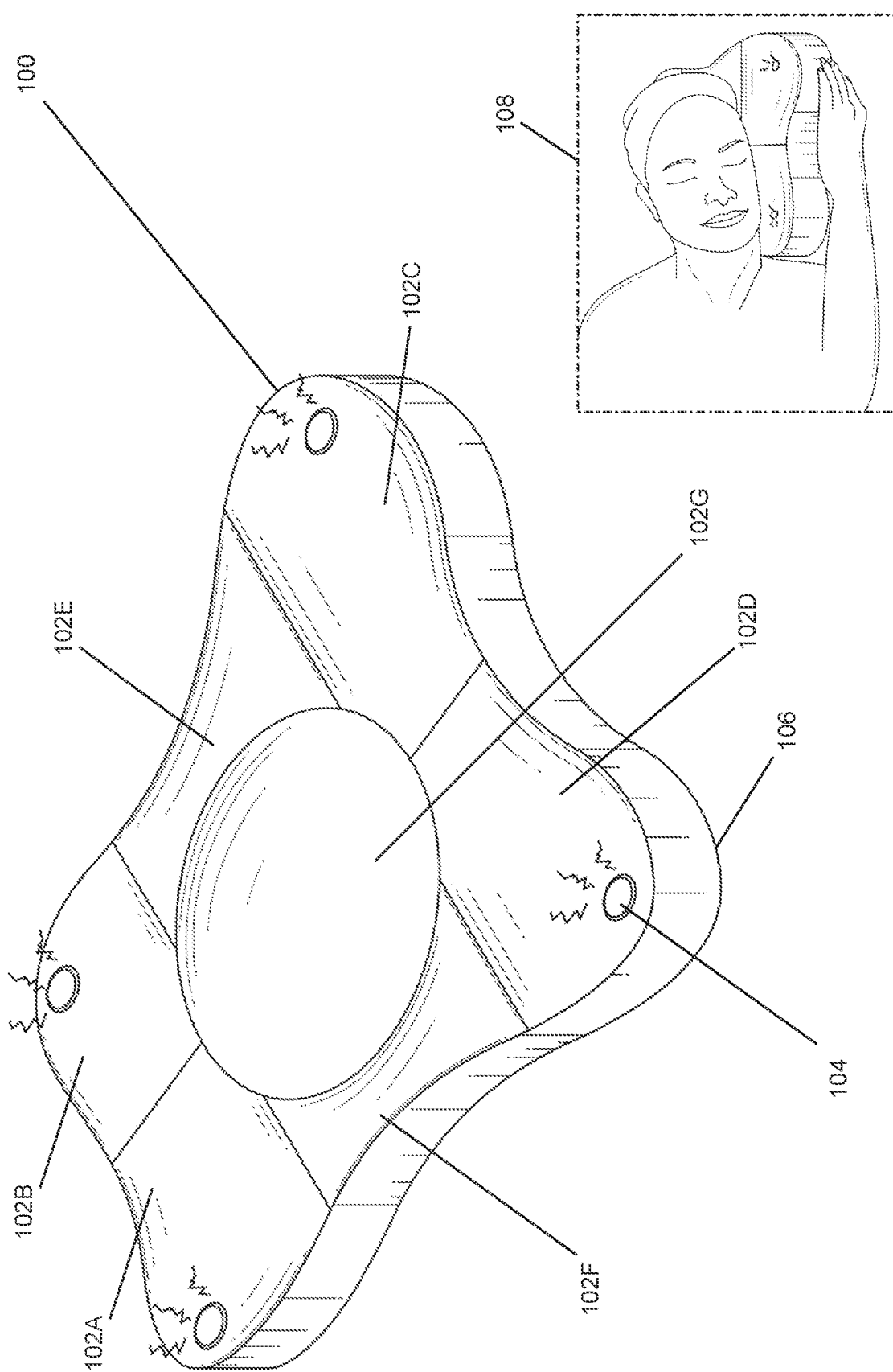
FIG. 1 illustrates a smart pillow that may be utilized in an automated sleep assistant, in accordance with one or more example embodiments of the present disclosure.

Certain implementations will now be described more fully below with reference to the accompanying drawings, in which various implementations and/or aspects are shown. However, various aspects may be implemented in many different forms and should not be construed as limited to the implementations set forth herein; rather, these implementations are provided so that this disclosure will be thorough and complete, and will fully convey the scope of the disclosure to those skilled in the art. Like numbers in the figures refer to like elements throughout. Hence, if a feature is used across several drawings, the number used to identify the feature in the drawing where the feature first appeared will be used in later drawings.

DETAILED DESCRIPTION

Example embodiments described herein provide certain systems, methods, and devices for automated sleep assistant devices. Automated sleep assistant devices as described herein are external to the user and has various benefits over internal implant devices, as they do not require a surgical procedure to be used, do not require the user to wear a mask or other coverings that the user may find obtrusive. Techniques described herein may be effective at improving user sleep while also being non-invasive and un-obtrusive to the user.

As described herein, an automated sleep assistant may refer to an apparatus or system that is used to identify adverse sleep-related conditions and provide for non-invasive mitigations. For example, Obstructive Sleep Apnea (OSA) is a type of sleep-related condition caused by weak muscles in the tongue and around the neck area. According to various embodiments described herein, an automated sleep assistant collects audio data of a user (e.g., human) while sleeping. While asleep, the user may make various utterances, such as snoring sounds, grunts, and the like. The collected audio data may be analyzed to determine whether the user has experienced various adverse sleep-related conditions, such as a blocked airway. In various embodiments, motion and/or force data are collected and analyzed to identify movement indicative of sleep disruptions. A combination of some or all of the data described above may be used to improve the accuracy of sleep assistant systems in detecting and mitigating adverse sleep-related conditions.

Different types of snoring or sound patterns may be indicative of different conditions. A first sound pattern may be correlated to a blocked airway, while a second sound pattern may be correlated with narrow sinus passages or compression at the throat due to fatty deposits or various other conditions. The audio data from the sleeping user may be processed using a machine-learning model that is trained to correlate different types of sleep sounds into different conditions. A simple method of doing this is using a machine-learning classifier. Upon detection of an adverse sleep-related condition, the automated sleep assistant may determine an appropriate mitigation. For example, if the sleep sounds are correlated with a blocked airway, the automated sleep assistant may determine that the stimulation of muscles in the tongue and around the neck area is an appropriate measure to take that restores the shape of the user's airway, will improve the user's breathing, decrease snoring, and ultimately improve the user's sleep quality. A pillow or pillow insert may be connected to a control device comprising a pump that is used to deliver stimulations to the user or to move the user's head to put it into a configuration where the airway is open naturally independent of muscle contractions. The stimulations may be applied externally to the user, meaning that there is no need for implants in the user, which often involves invasive, costly, and potentially risky medical procedures to be performed. Stimulations may be provided to the throat muscles as needed via micro-motions delivered by soft robotics, haptic stimulation or a combination thereof, or purely by changing the geometry of the head until the breathing sounds normalize.

The automated sleep assistant may comprise a pillow or pillow insert that is used to deliver external stimulations to the user as micro-motions, and/or macro-motions. A pillow may have sensors, air bladders, and haptic feedback devices embedded throughout the pillow. For example, a non-limiting, illustrative example of a pillow includes four air bladders located at the right, left, upper, and lower portions of the pillow, as well as an additional air bladder located within a well for cradling a user's head. Sensors within the pillow or from an external device, may be used to collect data regarding the user's motion, vibration, and pressure, and may be used to determine appropriate stimulations to provide to a user. For example, an air bladder underneath the user's neck can be inflated to change the angle of incline so that gravity naturally causes the user's soft palate and tongue into a position that facilitates an open airway. As a second example, stimulations applied from either side of the pillow that cause a user to roll to one side or another, which can also be used to address various adverse sleep-related conditions. For example, a user may have pain on only one side of their body—perhaps as a result of a surgical procedure on that side—and the automated sleep assistant is able to detect from sound and movement patterns of the user that the user frequently experiences pain when they turn on one side. When the automated sleep assistant detects (e.g., via pressure sensors located throughout the pillow) that the user has turned on that side, the automated sleep assistant may, in response, apply a stimulation to the user that acts as a nudge to push the user back to the other side. As a result, the user may experience improved sleep quality and decrease in pain during sleep, as users may not be consciously aware that their sleep movements are causing pain or discomfort.

Audio data and/or sensor data may be used to determine when and how to apply external stimulations to a user. For example, if the system sensed that a user increased the pressure on a left-side chamber of the pillow that resulted in snoring or painful grunts, that might cause air bladders on the chamber to inflate that chamber to encourage the user to roll back the other way. In some embodiments, a rocking motion may be achieved by alternatively inflating the left and right side chambers of a pillow to apply alternating lateral forces, upper and lower chambers of a pillow, and so forth. Accordingly, this approach of external stimulation and manipulation may be implemented as a non-invasive solution for mitigating adverse sleep-related conditions such as obstructive sleep apnea (OSA). This approach of using an automated sleep assistant that applies external actions to a user may be considered as a less intrusive alternative to implanted devices or continuous positive airway pressure (CPAP) machines.

The above descriptions are for purposes of illustration and are not meant to be limiting. Numerous other examples, configurations, processes, etc., may exist, some of which are described in greater detail below. Example embodiments will now be described with reference to the accompanying figures.

FIG. 1 illustrates a smart pillow 100 that may be utilized in an automated sleep assistant, in accordance with one or more example embodiments of the present disclosure.

The automated sleep assistant may comprise a pillow 100 or pillow insert that is used to deliver external stimulations to the user as micro-motions, macro-motions. A pillow may comprise multiple regions. In an illustrative embodiment, a pillow has four quadrants—a lower-left chamber region 102A, an upper-left chamber region 102B, upper-right chamber region 102C, lower-right chamber region 102D, upper-middle chamber region 102E, lower-middle chamber region 102F—and a well chamber region 102G. The regions may be described relative to the position of the user. For example, the user's neck may rest against the lower region of a pillow, whereas the top of the user's head rests on the bottom portion of the upper region, and the user's face is cradled within a well located in the middle portion of the pillow. A region may be a discretely sown pouch or chamber of the pillow that includes sensors, air bladder, haptic feedback devices, and the like. In some embodiments, the regions that include the sensors, air bladders, haptic feedback devices, etc. may include foam, feathers, or other materials typically found in pillows.

A chamber region may comprise one or more sensors, one or more inflatable air bladders, and one or more haptic feedback sensors. Sensors (not illustrated in FIG. 2) may be sensors embedded in the pillow to sense motion, vibration, and the pressure in each segment at a given time or they may be measured with external device such as a wrist or finger worn sensor, bed sensor or night stand sensor. Sensor data from multiple segments can be collected to determine a user's position. For example, pressure and position sensors in the left and right chamber regions can be used to determine whether the user is turned to one side or another when the pressure sensors on one side indicate the user is placing more pressure on one side than the other.

A chamber region may comprise one or more inflatable air bladders. Air bladders may be inflated via a pump that uses pressurized air to inflate the air bladder other means might include a pressurized air reservoir or other non-electric source. Pressurized air can be added or removed from an air bladder to modify the geometry of the pillow 100 to increase or decrease pressure on the neck or head muscles.

Stimulation devices such as haptic feedback device 104 depicted in FIG. 1 may be located throughout the pillow 100. In various embodiments, stimulation devices are located on the surface of a pillow or covered by a fabric material. In various embodiments, stimulation devices are used to supply targeted external stimulations or forces to specific muscles, whose location may be determined from sensors located throughout the pillow. Stimulations may be used to effect changes to body posture and to avoid apnea, snoring, or other adverse sleep-related conditions. An audio input device may be located on a bed stand or otherwise located nearby a user as she is sleeping. The audio input device may be used to collect audio data of sounds and utterances that the user makes while sleeping. Sensor data and/or video data (e.g., of a video camera) may be used to detect a user's movements. Data collected regarding how a user moves and utterances of the user may be used to determine an appropriate force to apply to the user to maximize sleep potential.

In various embodiments, air bladders and haptic feedback devices located throughout the pillow 100 may be independently activated or activated in combination with each other provide different types of actions that facilitate the user to move in a manner that improves their sleep potential. For example, an illustrative use case 108 depicted in FIG. 1 shows a user sleeping on pillow 100. In this illustrative use case 108, audio data may be collected from a separate audio input device (e.g., a smart assistant device on the user's night stand). Sounds and utterances made by the user may be collected by the audio input device and provided to a machine-learning model trained to identify sound patterns and identify whether sound patterns uttered by the user are correlated with an adverse sleep-related condition. For example, if a user begins snoring after they have turned on their left side, as depicted in illustrative use case 108, the automated sleep assistant may determine, within a control device, that the user should be turned to their other side. Based on this determination, the control device may send a signal to pillow 100 to activate haptic sensors located on the right chamber region, such as a sensor located in lower-left chamber region 102A or upper-left chamber region 102B. Haptic stimulations provided at the upper-right chamber region 102C or lower-right chamber region 102D, in some embodiments, cause the user to feel the sensation of a force being applied on the left side of the user's face (i.e., the side of the user's face that is touching the pillow), and in turn, the user may respond to the haptic feedback by turning over to their other side, similar to how a user may turn sides when the user is nudged or pushed when they start snoring, perhaps by the user's partner. In various embodiments, low frequency haptic stimulation can be used to provide the user with the perception of contact. In various embodiments, different frequencies of haptic stimulation may be applied. For example, a first frequency of haptic stimulation may be applied and can be repeated or the intensity or frequency can be changed to create a response if the user is not responding. In this way, different frequencies may be explored and learned by the automated sleep assistant, and certain frequencies may be identified as being more effective for an individual or certain population sets or subsets.

Pillow 100 may include a compliant casing such as foam or fabric casing 106. The casing may be made of any suitable material that is suitable for sleeping on, including soft foam or other materials known to one of ordinary skill in the art. In some embodiments, fabric or fibers in a mesh or plastic strut may be used as structural elements of pillow 100. In various embodiments, a recess or well can be located in a middle portion of pillow 100. The well may be a circular or oblong shape that accommodates the shape of a human head. The well may be a hallowed our or recessed portion of pillow 100 that is shaped to allow a user's head to sit within the well. The well may include a hole that extends all the way through the pillow, or may simply be a recessed or flat and deformable portion of pillow 100.

Figure 2:
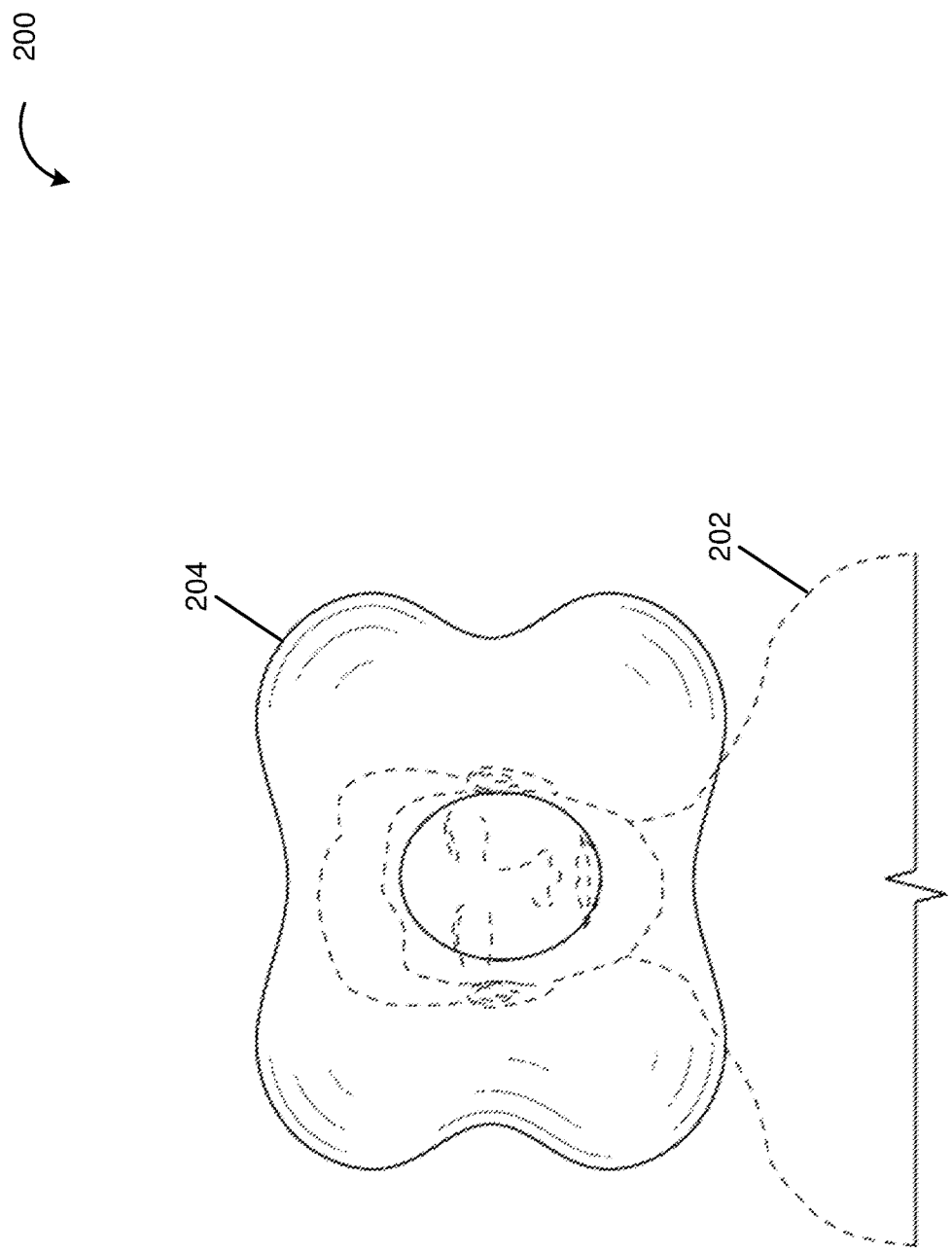
FIG. 2 illustrates a diagram of a person sleeping on pillow, in accordance with one or more example embodiments of the present disclosure.

FIG. 2 illustrates a diagram 200 of a person 202 sleeping on pillow 204, in accordance with one or more example embodiments of the present disclosure.

FIG. 2 illustrates, according to at least one embodiment, the interaction between a person 202 (sometimes referred to as a "user") and pillow 204. Person 202 is depicted in dotted lines and the outline of pillow 204 is depicted in solid lines. FIG. 2 depicts the relative scale of a pillow and user in a non-limiting, illustrative embodiment. Other sizes and shapes of pillow 204 are contemplated and within the scope of this disclosure. Pillow 204 may be in accordance with those described in connection with FIG. 1 and FIGS. 3-7.

In various embodiments, people experiencing obstructive sleep apnea (OSA), head and neck pain, and other sleep disturbances could potentially also benefit from a robotic sleep assist device. Pillow 204 may be attached to an external pump that is located in a housing that is sound and vibration isolating so the noise of pumping doesn't keep the user awake, which can be placed underneath a bed or nearby the user, so as to be able to deliver air pressure and to control the various chamber regions of pillow 204 while also being far enough away from the user's cars to avoid creating disturbances to the user's sleep arising from noise generated by the pump.

Pillow 204 may be used to implement a non-invasive automated sleep assistant. Other forms of non-invasive sleep assistants, such as pillow inserts, are also contemplated within the scope of this disclosure. This approach may be considered non-invasive in that it does not require the user to perform a surgical procedure to install an implant and also non-invasive in that it does not require the user to place a device in their mouth. For example, anti-snoring mouthpiece solutions may interfere with other conditions a user may have and may cause temporomandibular joint (TMJ) dysfunction after prolonged use.

Various adverse sleep-related conditions may be detected and mitigated, including but not limited to snoring and apnea. For example, sensors located on pillow 204 and audio input device may in concert determine that a person is waking up every time they turn on their left side. This may be due to the user having hurt their arm on that side, or that they are post-surgical, they have a spinal issue, or for a variety of other reasons. The collected sensor data can be used to detect changes from the pressure differentials in the pillow and their positions and correlate them to sleep events, and therefore determine an appropriate response when the user performs an action, is in a position, has a particular change in position, and so forth. For example, if the user rolls to one side, it may indicate that extending the user's neck more will result in better sleep potential. Several types of sleep-related problems may be solved using the framework described above. For example, two key disruptors of sleep are OSA and pain. Using the approach described above, pillow 204 could be dynamically adjustable to address pain and snoring. While pain is not directly measurable, sounds made by a user in their sleep may be correlated with pain and cause adverse sleep events as could motion signatures, which can be measured as a proxy that approximate pain experienced by a user when they are in certain positions or when they apply pressure to various regions of the pillow.

As an example, herpes zoster (shingles) is a type of viral infection that typically causes blisters to form on the left side or right side of a person's torso. In various embodiments, sensor data can be collected to determine when a user is turning or has turned on a side in which the user has blisters. In response to the collected data indicating such an event, haptic feedback or pillow forces may be applied to nudge or push the user back to the other side. In some embodiments, an inflatable air bladder is inflated to turn the user to the other side. In this way, the amount of pain a user experiences during sleep from subconscious tossing and turning may be reduced or eliminated.

Another example in which sleep potential may be improved is for pregnant women, who may sleep preferentially on one side. In various embodiments, sensors can be used to detect the movement and position of the user, and stimulations may be supplied to ensure that a user stays in a position or in response to a change in position where the user flips to the other, non-preferential side. Users may be able to configure the pillow 204 to have a preferential side, for example, through a mobile application that stores user-specific settings for an automated sleep assistant.

While a pillow is depicted in FIG. 2, other designs are contemplated within the scope of this disclosure. For example, rather than including sensors and stimulation devices within a pillow, a pillow insert may instead be used so that a user is able to continue sleeping on the pillow of their choice. Accordingly, in various embodiments, an automated sleep assistant may comprise a pillow insert that slides into a pillow cover. In some cases, a pillow case with a separate zipper compartment for the pillow insert may be utilized to ensure that the pillow insert does not slide out of position while the user is sleeping.

Figure 3:
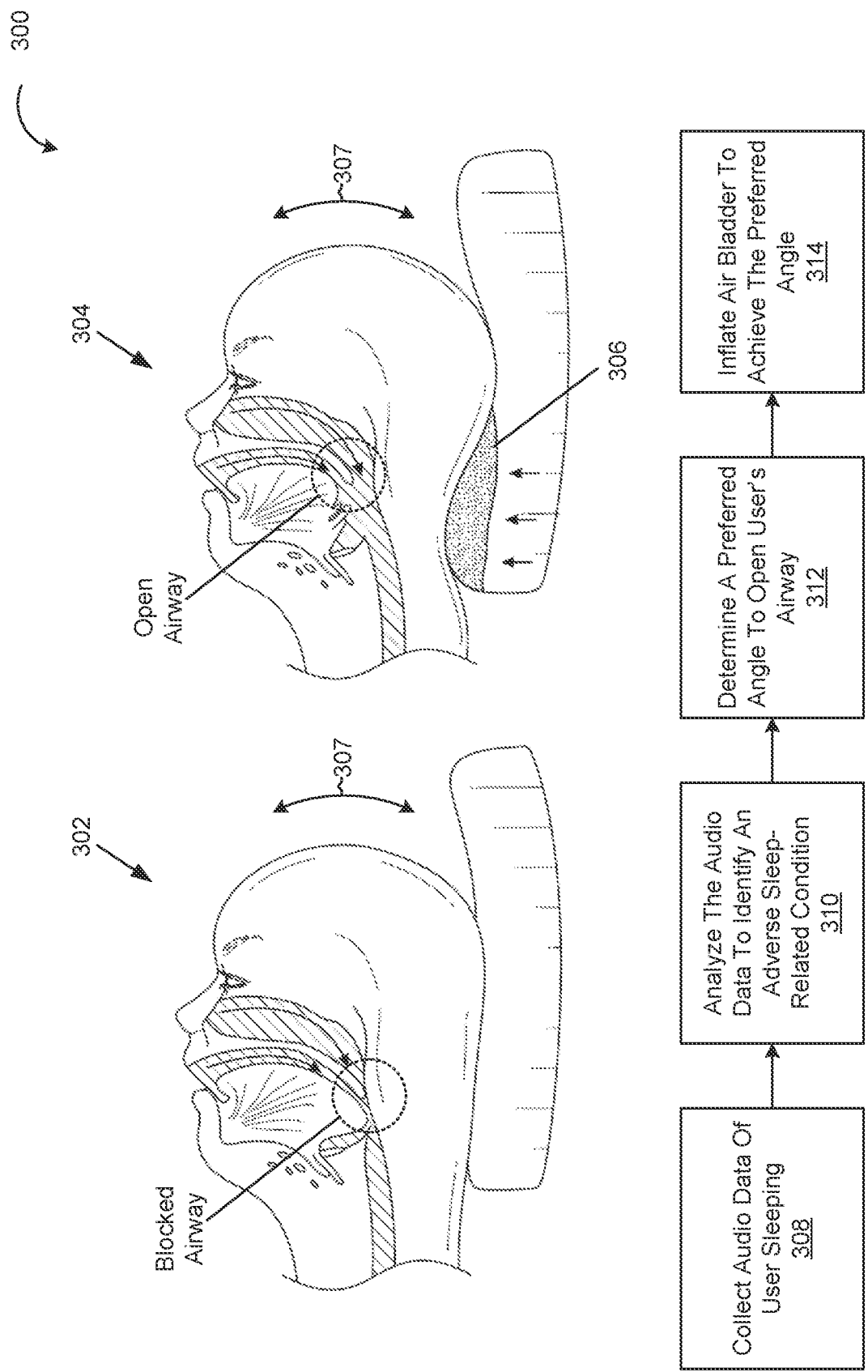
FIG. 3 illustrates a diagram of an illustrative use case of an automated sleep assistant that improves the user's breathing and or comfort during sleep, in accordance with one or more example embodiments of the present disclosure.

FIG. 3 illustrates a diagram 300 of an illustrative use case of an automated sleep assistant that improves the user's breathing during sleep, in accordance with one or more example embodiments of the present disclosure. Pillows described in connection with FIG. 3 may be in accordance with those discussed elsewhere, such as with embodiments in FIGS. 1, 2, and 4-7.

Illustration 302 depicts a user with a blocked airway. Illustration 302 depicts how the tongue and soft palate are relaxed. This results in a configuration where the tongue presses at the back of the soft palate and causes the user's airway to be closed. This may result in snoring or other unpleasant sound utterances from the user. During sleep apnea, the tongue is relaxing and/or the soft palate is relaxing, resulting in a blocked or partially obstructed airway that may adversely impact the user's sleep potential, cause snoring that reduces the sleep quality of those around the user, and so forth.

Illustration 304 depicts a mitigation to open a user's airway. The mitigation may be implemented in response to detecting a blocked airway, for example, as depicted in illustration 302. In various embodiments, an inflatable air bladder 306 is used to lift the back of the neck and stimulate muscles located at the back of the neck to restore the shape of the airway. With sleep apnea, a key mechanism relating to whether the user's airway is locked or opened is the muscle tone at the base of the tongue, where the muscles tether it to the base of the chin. Apnea occurs during sleep because these muscles relax.

Inflatable air bladder 306 may be used to change the vector of force from gravity so that it naturally pushes the two users to a position where the airway is unobstructed. Other types of stimulations may be used to jostle the user and provide direct muscle stimulation. In this way, the air bladder 306 may be inflated so that the head is tipped 307 backward to an angle where the tongue is held in a position that keeps the user's airways open.

Gravity, depending on the angle of the user's head, may contribute to the user's airway being blocked or opened. This may be due to a combination of geometry and muscle action, wherein when the user's muscles are relaxed, the force of gravity causes the user's soft palate and tongue to rest in a particular configuration that may or may not result in the user's airway being blocked.

Sensors located on a pillow may be used to determine, based on the relative amount of pressure exerted on different chamber regions of the pillow, an angle at which the user's head rests. This angle may be preferentially adjusted, tipping the head back ward and/or forward 307, to achieve a more desirable angle that allows the tongue and soft palate to rest in a position where the user's airway remains open.

In at least one embodiment, an automated sleep assistant collects audio data of user sleeping 308. This audio data may be collected by a separate device from the pillow, for example, an audio sensor that is located on a night stand next to the user. The collected audio data may be transmitted over a network, such as the Internet, via an encrypted connection to a server that processes the audio.

In various embodiments, software locally or on a cloud based system analyzes the audio data to identify an adverse sleep-related condition 310. The analysis may be performed using a machine-learning model that is trained to determine whether the sound patterns uttered by the user are indicative of an adverse sleep-related condition such as apnea. The sleep pattern of a user in the position depicted in illustration 302 may indicate that the user has a blocked airway. Sensors on the pillow may be used to determine the angle at which the user's head is resting. The software may determine a preferred angle to open user's airway 312. The ideal angle may be determined based on sleep studies of populations of individuals, and may be augmented or superseded by individualized information for each user. For example, if historical data indicates that the user's airway was previously opened at a certain angle and did not result in subsequent adverse events, then that angle may be used as the preferred angle.

A control unit may use a pump to inflate an appropriate air bladder to achieve the preferred angle 314. Inflating the air bladder 306 changes the angle of attack so that gravity naturally tends the user's airway to open so that the tongue doesn't fall against the soft palate. The pillow may be attached via an air tube to a pump, which can be placed under the user's bed so that noise generated by the pump's operation does not disrupt the user's sleep. As the user sleeps, multiple bladders located across the pillow may be inflated and deflated to change the configuration of the pillow to provide pressure to appropriate regions of the neck or head. For example, if a user is snoring while sleeping on one side, the air bladders on that side may be inflated to get the user to roll over on their other side.

Stimulation and micro-motions may be provided through haptics to cause users to shift their positions a little and their muscles will fire and they will open their airways again. Micro-motions may refer to small forces applied to muscles that cause the muscles to fire and effect larger, macro-level changes. In various embodiments, stimulation devices such as haptic feedback devices are used to deliver micro-stimulations to muscles, micro-move the body, where those micro-motions cause the muscles themselves to perform larger movements, such as rolling over from one side to another.

In various embodiments, different types of stimulations can be delivered to user. For example, air bladders may be used to provide upward or generally upward forces at their specific locations throughout the pillow, haptic stimulation can be delivered from haptic devices located throughout the pillow, and so forth. Combinations of nudges to push the user in a direction (e.g., inflating an air bladder), micro-stimulations to cause certain muscles to contract, etc. may be used in combination with each other or individualized based on learned user responses. Different levels of user responsiveness may be learned based on users' varying geometries, fat, muscle tone, etc. Machine-learning models may be trained to collect data regarding how responsive a user is to various types of stimulations, micro-motions, etc., and determine individualized mitigation strategies. In some embodiments, users can personally override and manually tune the way in which different stimulations are applied. For example, a user may find certain types of stimulation unpleasant and deactivate them from use.

Figure 4:
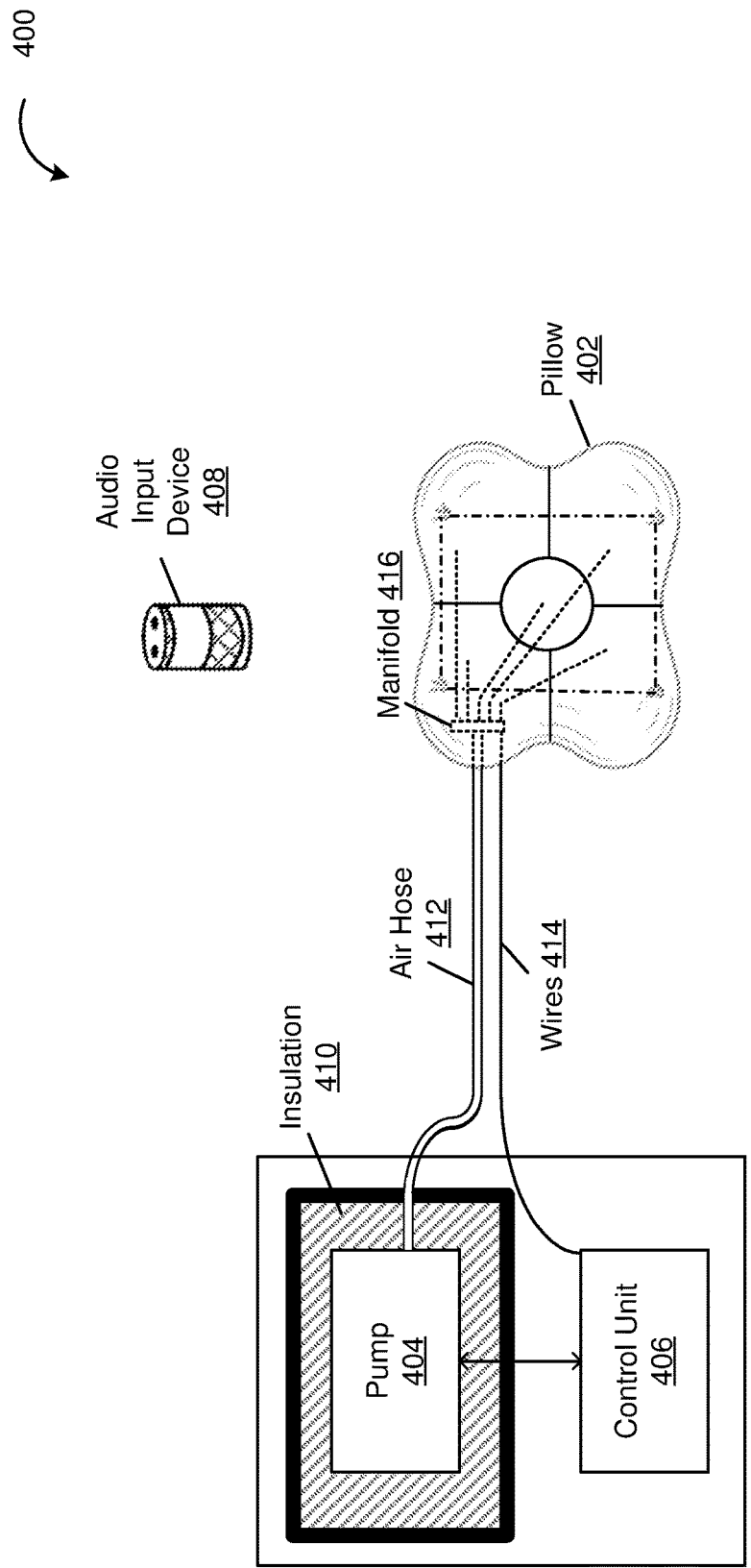
FIG. 4 illustrates a diagram of an automated sleep assistant system, in accordance with one or more example embodiments of the present disclosure.

FIG. 4 illustrates a diagram 400 of an automated sleep assistant system, in accordance with one or more example embodiments of the present disclosure. A system as described herein may comprise a pillow 402, a base unit device comprising a pump 404 and control unit 406, and audio input device 408. The base unit device may have insulation 410 surrounding the pump 404 to dampen or reduce noise generated by the pump 404.

Audio input device 408 may refer to a discrete device such as a portable smart digital assistant or other suitable device. In some cases, a smartphone or tablet can be used as an audio input device, with permission from the user being granted to use the device as such. Pillow 402 includes air bladders, haptic feedback devices, and other types of stimulators that can be used to stimulate and exercise certain muscles that may be used to reduce the incidence of sleep apnea, snoring, or other adverse sleep-related conditions.

Audio input device 408 may be used to collect people's sleep snoring and other sleep related sounds. Audio input device 408 may be placed on a night stand or other location near the user so that sleep sounds may be clearly captured by audio input device 408. In some embodiments, audio input device 408 is communicatively connected to a server or service provider and is able to perform audio processing algorithms on sound data collected from the user while sleeping. Such a process can be performed locally on the device or remotely in the cloud. In some embodiments, audio input device 408 is connected to control device 406 (e.g., via a local network), and the control device processes sleep audio to detect sleep-related events.

In various embodiments, pillow 402 comprises sensors, air bladders, haptic feedback devices, and so forth, for example, as described in connection with FIGS. 1-3 and 4-7. Pillow 402 may be connected to pump 404 via an air hose 412 going into a manifold to actuate the different chambers. The pump may be located within a sound-dampening housing made of any soundproof or sound dampening material.

Pump 404 may refer to a pump, motor, or any other suitable system that can be used to inflate and/or deflate the air bladders of pillow 402. Pressurized air may be delivered via air hose 412 based on control signals provided by control unit 406. Pump 404 may be used to drive different amounts of air pressure to a plurality of air bladders located throughout the pillow 402. Control unit 406 may refer to electronic circuitry such as a computer system or embedded electronic system that has one or more processors and memory that is used to store executable instructions to control various aspects of the pillow 402. For example, control device 406 may be used to control pump 404 to increase and/or decrease the air in air bladders located in various chambers of the pillow 402. In some embodiments, control unit 406 is connected to pillow 402 to control haptic feedback devices located throughout pillow 402 to provide haptic stimulation, for example, when such stimulations are determined to be appropriate to an adverse sleep-related event that a user has experienced.

Wires 414 may refer to electrical wires that are used to carry electrical signals from control unit 406 to pillow 402. In some embodiments, wires 414 are used to communicatively couple control unit 406 to one or more sensors and/or stimulators of pillow 402. For example, control unit 406 may be used to send electrical signals to pillow 402 to fire feedback devices such as haptic feedback devices at specific locations of the pillow 402, for example, to cause the user to shift in a particular desired manner so as to improve sleep potential. While shown separately in FIG. 4, air hose 412 and wires 414 may be sleeved together and have shared or adjacent connecting ports to pillow 402, which may provide the user with a simpler setup, as the hose and wires are bundled together such that communication between the control unit and pillow sensors are bi-directional. Wires 414 may be used to supply power to various sensors and stimulators located throughout pillow 402. For example, FIG. 4 depicts four stimulator devices that are supplied power through wires 414 that connect to pillow 402 and are integrated internal to the pillow so as to not protrude or be otherwise visible or felt to the user while sleeping, as symbolized by the dotted-dashed lines. Wire may be connected to the manifold and bidirectional between the pump and control unit.

In an alternative embodiment, wireless mechanisms are used to connect control unit 406 to pillow 402. For example, in some embodiments pillow 402 includes a Bluetooth wireless receiver and/or transmitter that can be paired with control unit 406 to facilitate one-way or two-way communications. For example, sensors located throughout pillow 402 may collect pressure, location, motion, etc. data while the user is sleeping and transmit such data to control unit 406 They can be wired internally to a microcontroller that communicates via wireless (e.g., Bluetooth) to the sensor module or an external cloud or another device. In some embodiments, wireless receives located in pillow 402 receive commands to apply an action, such as applying an external pressure to the user, causing the user to apply an external pressure (e.g., through micro-stimulations or haptics), applying a temperature adjustment, and so forth.

Manifold and associated valving 416 may refer to a component that regulates the flow of pressurized air to a plurality of inflatable air bladders located throughout pillow 402. While a manifold is depicted in FIG. 4, any suitable valve, multiplexer, or other air flow control regulation mechanism may be utilized and is contemplated in the scope of this disclosure. Manifold 416 may be used to regulate the amount of pressure between pump 404 and a plurality of inflatable air bladders that can be independently controlled. For example, control unit 406 may be used to determine an amount of pressure that should be delivered to each of the air bladders of pillow 402, pump 404 is used to deliver pressurized air, and manifold 416 is used to deliver the desired amount of pressure to each of the air bladders. As denoted by the dotted lines, manifold 416 may be integrated internally to the pillow so as to not protrude or be otherwise visible or felt to the user while sleeping.

In various embodiments, the automated sleep assistant system depicted in FIG. 4 is used to provide active feedback in response to snoring, apnea, or other adverse sleep-related events, which may be identified through the analysis of user sounds collected from audio input device 408 and from sensors in the pillow or external sleep related sensing such as in a bed or a bedside motion detecting device. Sound information and/or sensor information may be used to determine whether to apply micro-motions, macro-motions, haptic stimulation and other types of muscle stimulation or auditory stimulation, or a combination thereof. The automated sleep assistant may operate in a dynamic, non-invasive manner.

In various embodiments, data regarding how often the user wakes up each night as well as other sleep-state information can be collected to determine whether the user meets certain clinical requirements to be diagnosed with a sleep-related condition such as OSA. This data can be collected, aggregated across population sets, and used by diagnosticians and clinicians to study different indications of sleep disruption.

Figure 5:
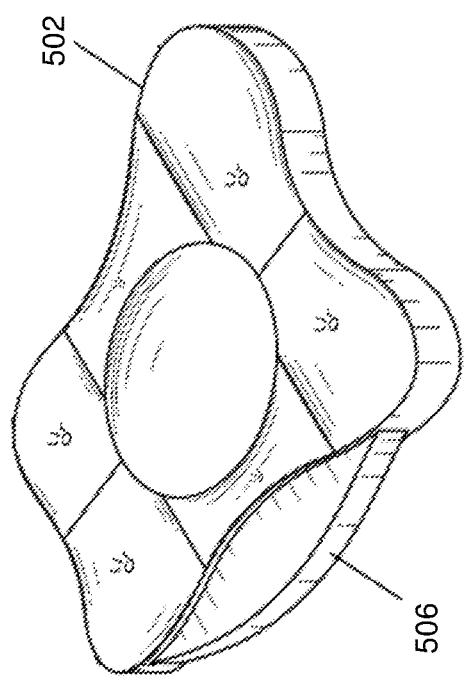
FIG. 5 illustrates a diagram of example pillow attachments, in accordance with one or more example embodiments of the present disclosure.
Figure 5:
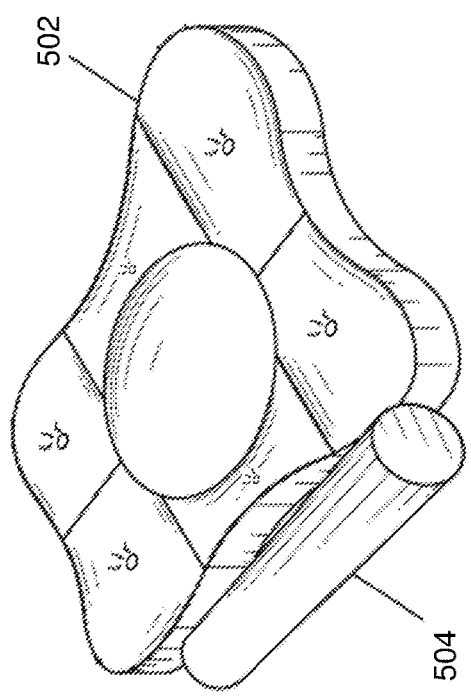

FIG. 5 illustrates a diagram 500 of example pillow attachments, in accordance with one or more example embodiments of the present disclosure. Pillow 502 depicted in FIG. 5 may refer to a pillow as discussed in connection with FIGS. 1-4. In various embodiments, pillow 502 can be designed to work in concert with various add-ons, such as first pillow add-on 504 and second pillow add-on 506. For example, a pillow add-on may be utilized by people that have long necks or have personal geometries that make using pillow 502 by itself more difficult. Persons with neck pain or require more support under the neck or back region may benefit from the use of a pillow add-on.

Pillow 502 may comprise five chambers or pockets—a chamber in an upper, lower, left, and right region of the pillow, and a fifth pocket underneath a well in the middle portion of the pillow that can be used to lift or tip the user's head. Add-ons, such as those depicted in FIG. 5, may be useful attachments that a user with a long neck may find helpful and would be able to be independently attachable and detachable.

As depicted in FIG. 5, stimulators or feedback devices may be located throughout pillow 502. For example, in at least one embodiment, pillow 502 comprises seven regions—an upper-left region, lower-left region, upper-right region, lower-right region, upper-middle region, lower-middle region, and a good region located underneath a recess for cradling a user's head. Each of these regions may have a stimulator or haptic device located in the central portion of their respective regions. Sensors, stimulators, feedback devices, etc., may be located throughout a pillow.

Figure 6:
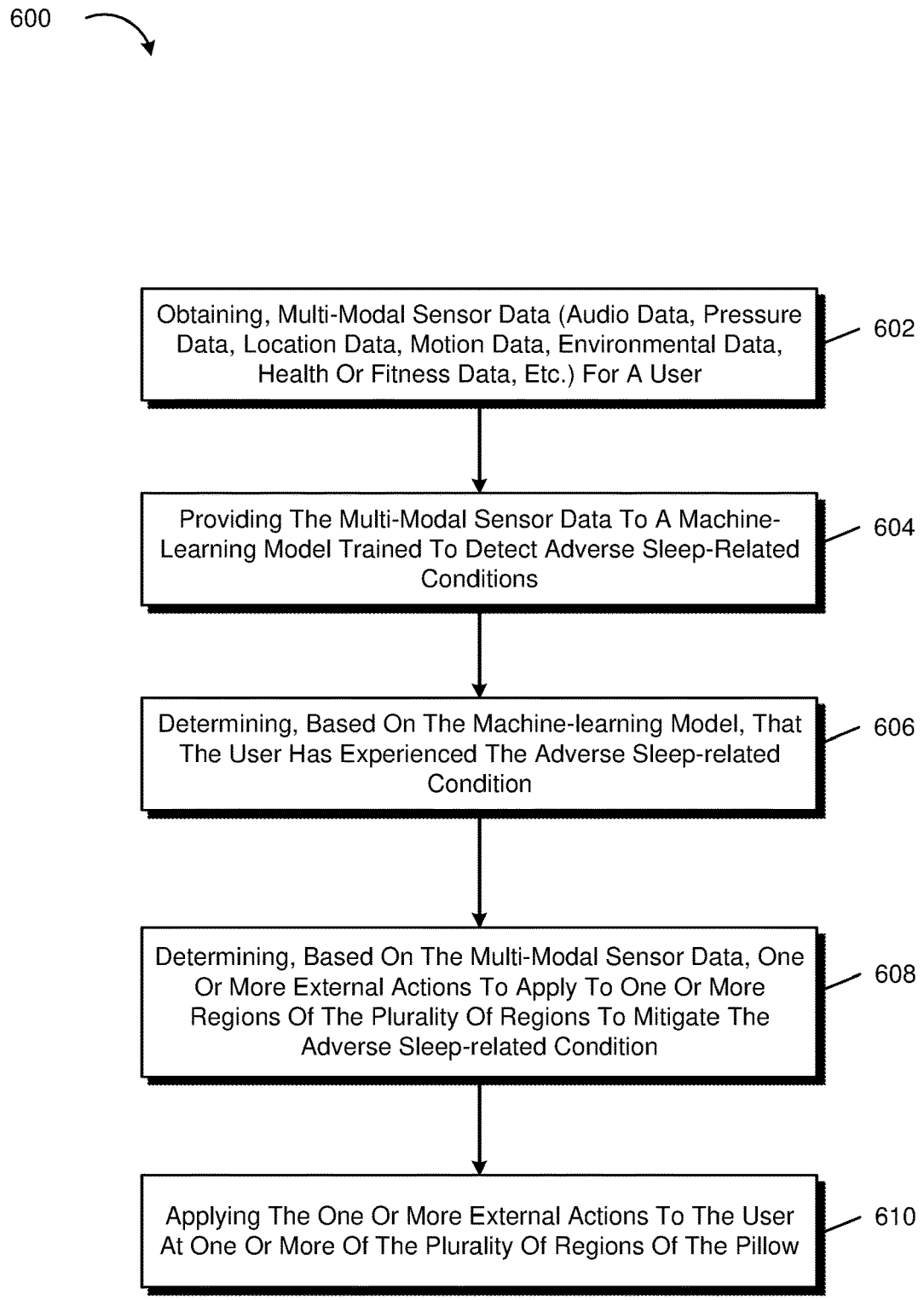
FIG. 6 shows an illustrative example of a process for sensing an adverse sleep-related event and providing targeted stimulations to improve sleep potential, in accordance with one or more example embodiments of the present disclosure.

FIG. 6 shows an illustrative example of a process 600 for sensing an adverse sleep-related event and providing targeted stimulations to improve sleep potential, in accordance with one or more example embodiments of the present disclosure. In at least one embodiment, some or all of the process 600 (or any other processes described herein, or variations and/or combinations thereof) is performed under the control of one or more computer systems that store computer-executable instructions and may be implemented as code (e.g., computer-executable instructions, one or more computer programs, or one or more applications) executing collectively on one or more processors, by hardware, software, or combinations thereof. The code, in at least one embodiment, is stored on a computer-readable storage medium in the form of a computer program comprising a plurality of computer-readable instructions executable by one or more processors. The computer-readable storage medium, in at least one embodiment, is a non-transitory computer-readable medium. In at least one embodiment, at least some of the computer-readable instructions usable to perform the process 600 are not stored solely using transitory signals (e.g., a propagating transient electric or electromagnetic transmission). A non-transitory computer-readable medium does not necessarily include non-transitory data storage circuitry (e.g., buffers, caches, and queues) within transceivers of transitory signals. Process 600 may be implemented in the context of various systems and methods described elsewhere in this disclosure, such as those discussed in connection with FIGS. 1-5 and 7. In at least one embodiment, process 600 or a portion thereof is implemented by an automated sleep assistant system. Process 600 may be implemented in the context of mitigating an adverse sleep-related condition for a user. The user may be a user that is determined to be sleeping based on movement and/or heart-rate patterns. In some cases, the user is a user that is trying to fall asleep but is unable to due to an adverse sleep-related condition. In some embodiments, rocking micro-movements and/or soothing audio is played to help the user relax and fall asleep. Rocking micro-movements may comprise alternating first and second micro-movements along two different directions (e.g., left-right and/or up-down movements).

In at least one embodiment, process 600 comprises a step for obtaining 602 multi-modal sensory data for a user. Multi-modal sensors may include one or more of: audio data, pressure data, location data, motion data, environmental data, health or fitness data, combinations thereof, and so forth. Multi-modal sensor data may be collected from a single device or from multiple discrete devices, as appropriate for the type of data being collected. For example, pressure, location, and motion data may be collected from sensors located on a pillow; audio data may be collected from an audio input device located on the user's night stand or other location that is positioned appropriately for collecting sleep sound data; environmental data such as ambient temperature or user temperature may be collected from a thermostat or temperature sensors located on the bed, pillow, health-tracking device the user is wearing, and so forth; health or fitness data may be collected by a fitness tracker device that the user wears while sleep.

The audio data may be collected from an audio input device. For example, a sleep assistant device or smart assistance device may be placed on a night stand next to or in proximity to a user to record sleep sounds from the user. Different sound patterns may be correlated to different sleep-related conditions through machine-learning and by using various classification models known in the art. In some embodiments, a multi-modal sensor collection device is used to collect audio data, environmental data, location or motion data, and so forth. For example, a multi-modal collection device may be a small, discrete device that a user can place on her/his night stand. The device may collect audio data using a microphone, motion and/or location data using a laser imaging, detection, and ranging (LIDAR) device, and so forth. In some embodiments, a network-connected thermostat is used to collect ambient temperature. In some embodiments, a temperature sensor located on the pillow or on a wearable health-tracking device is used to collect temperature data of the user.

In at least one embodiment, process 600 comprises a step for providing 604 the multi-modal sensor data to a machine-learning model trained to detect adverse sleep-related conditions. Multi-modal sensors may include one or more of: audio data, pressure data, location data, motion data, environmental data, health or fitness data, combinations thereof, and so forth. Machine-learning models in this context may be trained using audio and/or sensors, including video and/or LIDAR data that is provided through a sleep study wherein experts in the field review training audio/video and annotate sleep events in the timeline or using traditional devices that measure brain waves to identify the phases of sleep and correlating them to sounds and/or other sensor data. For example, various sleep-related disturbances may be recorded and annotated. A machine-learning model (e.g., classification model) may be trained on data labeled by sleep experts. Different types of events may be recorded as being adverse to the user's sleep. For example, if motion and/or location information is collected and processed to determine a person rolled over and got apnea or started to snore, that may be labeled as an adverse event. A taxonomy of labeling may be created that describes different adverse sleep-related conditions. Machine-learning models, as described herein, may be trained based on a training data set that is provided to a service provider that collects sleep data and processes the sleep data to determine when an adverse event has occurred. In some embodiments, personal health devices, such as health bands, smart watches, and the like, may be used to record various information to aid in the detection of adverse sleep events. These devices may be used to record biometric information of the user, such as heart rate information that may be used to determine whether a user was adversely affected by a sleep event.

In at least one embodiment, process 600 comprises a step for determining 606, based on the machine-learning model or heuristic model, that the user has experienced the adverse sleep-related condition. A classification model may be used to determine whether multi-modal sensor data is indicative of an adverse sleep-related event. If such an event is detected, the machine-learning model may identify the type of adverse event, which may be logged and recorded so that the user may review their sleep history at a later point in time. For example, the user's sleep quality may be recorded and presented to the user in a graphical user interface on a tablet or smartphone device showing a timeline of when the user fell asleep, when certain events occurred, and so forth. In some embodiments, the graphical user interface may display actions performed by the automated sleep assistant, such as providing stimulations to the user that caused them to turn over. Users may be assigned a sleep score based on the quality of their sleep, which may be based on how many adverse events the user experienced, how well the user responded to stimulations and micro-motions provided by the automated sleep assistant system, and so forth.

In at least one embodiment, process 600 comprises a step for determining 608, based on the multi-modal sensor data, one or more external actions to apply (step 610) to one or more regions of the plurality of regions to mitigate the adverse sleep-related condition. In some embodiments, the machine-learning model uses sound patterns and/or sensor data to infer one or more external actions to apply to the user that move the user or cause the user to move in a way that mitigates the adverse sleep-related condition. The external action may, for example, be used to cause the user to perform a macro-motion, such as rolling to a side. The external action may be to inflate an air bladder and/or stimulate muscles to tip the head upwards or downwards so that the head is at an angle in which the soft palate and tongue muscles rest in a position that does not block the user's airway. In some embodiments, haptic feedback is provided as a mechanism for applying muscle stimulation to move the user in a specific intended manner. A pillow or pillow insert may include stimulation devices in various quadrants, regions, chambers, etc., and the machine-learning model may provide a set of parameters indicating how each of them is to be adjusted or for some to remain unused. In some embodiments, a sequence of motions are to be performed, such as by alternatively inflating a first air bladder on a right-hand side and a second air bladder on a left-hand side—for example, to stimulate the user to slowly rock from one side to another. Haptics may be used to perform various techniques described herein. The external action may include heating or cooling of the user. For example, multi-modal sensor data may be used to monitor the temperature of a sleeping user. The temperature may be collected from a wearable health-tracking device, from temperature sensors located on the pillow, from an infrared thermometer that measures black-body radiation emitted by the sleeping user, from an ambient temperature sensor such as a thermostat and so forth. Based on one or more temperature measurements or a combination thereof, it may be determined that cooling or heating should be applied to improve sleep potential. In some embodiments, heating or cooling is applied by control of a heating or cooling device integrated into the pillow. A current may be run through a heating element integrated into the pillow, mattress, blanket, or various other apparatuses that the user is in contact with. In some embodiments, a thermostat is adjusted to apply heating or cooling of the ambient temperature.

One or more operations of the methods, process flows, or use cases of FIGS. 1-7 may have been described above as being performed by a user device, or more specifically, by one or more program module(s), applications, or the like executing on a device. It should be appreciated, however, that any of the operations of the methods, process flows, or use cases of FIGS. 1-7 may be performed, at least in part, in a distributed manner by one or more other devices, or more specifically, by one or more program module(s), applications, or the like executing on such devices. In addition, it should be appreciated that processing performed in response to execution of computer-executable instructions provided as part of an application, program module, or the like may be interchangeably described herein as being performed by the application or the program module itself or by a device on which the application, program module, or the like is executing. While the operations of the methods, process flows, or use cases of FIGS. 1-7 may be described in the context of the illustrative devices, it should be appreciated that such operations may be implemented in connection with numerous other device configurations.

The operations described and depicted in the illustrative methods, process flows, and use cases of FIGS. 1-7 may be carried out or performed in any suitable order, such as the depicted orders, as desired in various example embodiments of the disclosure. Additionally, in certain example embodiments, at least a portion of the operations may be carried out in parallel. Furthermore, in certain example embodiments, less, more, or different operations than those depicted in FIGS. 1-7 may be performed.

Although specific embodiments of the disclosure have been described, one of ordinary skill in the art will recognize that numerous other modifications and alternative embodiments are within the scope of the disclosure. For example, any of the functionality and/or processing capabilities described with respect to a particular device or component may be performed by any other device or component. Further, while various illustrative implementations and architectures have been described in accordance with embodiments of the disclosure, one of ordinary skill in the art will appreciate that numerous other modifications to the illustrative implementations and architectures described herein are also within the scope of this disclosure.

Certain aspects of the disclosure are described above with reference to block and flow diagrams of systems, methods, apparatuses, and/or computer program products according to example embodiments. It will be understood that one or more blocks of the block diagrams and flow diagrams, and combinations of blocks in the block diagrams and the flow diagrams, respectively, may be implemented by execution of computer-executable program instructions. Likewise, some blocks of the block diagrams and flow diagrams may not necessarily need to be performed in the order presented, or may not necessarily need to be performed at all, according to some embodiments. Further, additional components and/or operations beyond those depicted in blocks of the block and/or flow diagrams may be present in certain embodiments.

Accordingly, blocks of the block diagrams and flow diagrams support combinations of means for performing the specified functions, combinations of elements or steps for performing the specified functions, and program instruction means for performing the specified functions. It will also be understood that each block of the block diagrams and flow diagrams, and combinations of blocks in the block diagrams and flow diagrams, may be implemented by special-purpose, hardware-based computer systems that perform the specified functions, elements or steps, or combinations of special-purpose hardware and computer instructions.

The examples presented herein are not meant to be limiting.

Figure 7:
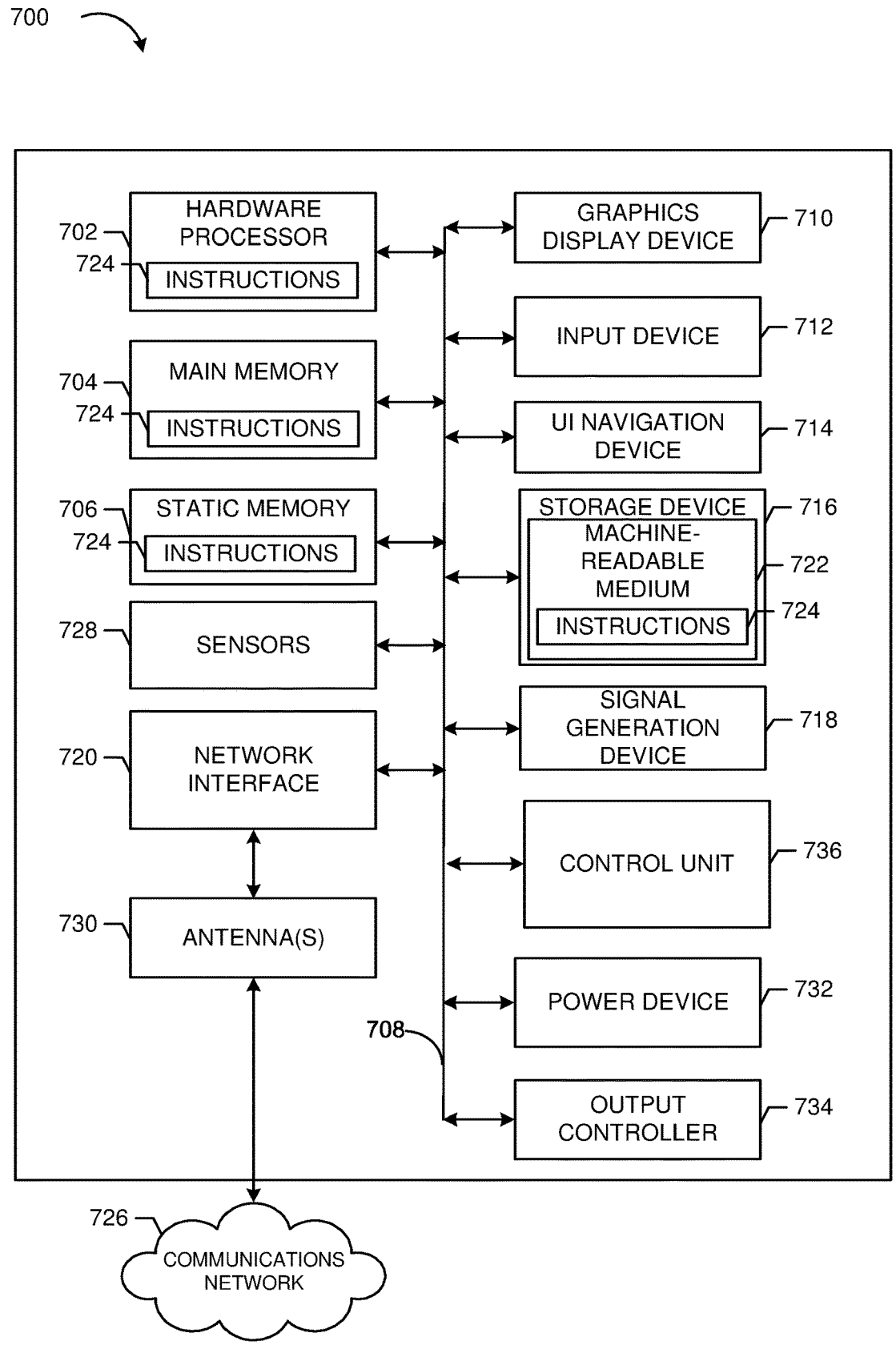
FIG. 7 illustrates a block diagram of an example machine upon which any of one or more techniques (e.g., methods) may be performed, in accordance with one or more example embodiments of the present disclosure.

FIG. 7 illustrates a block diagram of an example of a machine 700 (e.g., implemented in whole or in part in the context of embodiments described in connection with other figures. In some embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in Wi-Fi direct, peer-to-peer (P2P) (or other distributed) network environments. The machine 700 may be a wearable device or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), or other computer cluster configurations. In some embodiments, firmware on a device such as a mobile device is used. Sensor data may be determined or calculated off of a local device and loaded into firmware on the device so that they may react more quickly to sleep signals. In some embodiments, behaviors can be reset or extended periodically, which can be used to reduce power-usage and/or bandwidth.

Examples, as described herein, may include or may operate on logic or a number of components, modules, or mechanisms. Modules are tangible entities (e.g., hardware) capable of performing specified operations when operating. A module includes hardware. In an example, the hardware may be specifically configured to carry out a specific operation (e.g., hardwired). In another example, the hardware may include configurable execution units (e.g., transistors, circuits, etc.) and a computer readable medium containing instructions where the instructions configure the execution units to carry out a specific operation when in operation. The configuring may occur under the direction of the execution units or a loading mechanism. Accordingly, the execution units are communicatively coupled to the computer-readable medium when the device is operating. In this example, the execution units may be a member of more than one module. For example, under operation, the execution units may be configured by a first set of instructions to implement a first module at one point in time and reconfigured by a second set of instructions to implement a second module at a second point in time.

The machine (e.g., computer system) 700 may include any combination of the illustrated components. For example, the machine 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a power management device 732, a graphics display device 710, an alphanumeric input device 712 (e.g., a keyboard), and a user interface (UI) navigation device 714 (e.g., a mouse). In an example, the graphics display device 710, alphanumeric input device 712, and UI navigation device 714 may be a touch screen display. The machine 700 may additionally include a storage device (e.g., drive unit) 716, a signal generation device 718, and a network interface device/transceiver 720 coupled to antenna(s) 730. The machine 700 may include an output controller 734, such as a serial (e.g., universal serial bus (USB), parallel, or other wired or wireless (e.g., infrared (IR), near field communication (NFC), etc.) connection to communicate with or control one or more peripheral devices (e.g., a printer, a card reader, other sensors, etc.)).

The storage device 716 may include a machine readable medium 722 on which is stored one or more sets of data structures or instructions 724 (e.g., software) embodying or utilized by any one or more of the techniques or functions described herein. The instructions 724 may also reside, completely or at least partially, within the main memory 704, within the static memory 706, or within the hardware processor 702 during execution thereof by the machine 700. In an example, one or any combination of the hardware processor 702, the main memory 704, the static memory 706, or the storage device 716 may constitute machine-readable media.

While the machine-readable medium 722 is illustrated as a single medium, the term "machine-readable medium" may include a single medium or multiple media (e.g., a centralized or distributed database, and/or associated caches and servers) configured to store the one or more instructions 724.

Control unit 736 may refer to a control unit that may be used to control a motor and/or perform various functionalities described in connection with an automated sleep assistant system. For example, control unit 736 may be utilized to communicate with a server. The server may receive audio data from an audio input device and use a machine-learning algorithm to identify adverse sleep-related events from sound patterns detected in the sounds and utterances that a user subconsciously makes while sleeping. The server may send machine @@00 a message over a network with parameters that indicate one or more stimulations, micro-motions, etc. that should be applied in response to an adverse sleep-related event being detected. For example, the machine-learning model may identify one or more stimulation devices such as haptic feedback devices that should be activated, the strength or frequency at which they should be activated, and other configurable parameters of the smart pillow. Machine 700 may receive the message from the server and use control unit 736 to cause a pump to inflate an air bladder, send an electronic signal that causes one or more stimulation devices to fire, and so forth.

Various embodiments may be implemented fully or partially in software and/or firmware. This software and/or firmware may take the form of instructions contained in or on a non-transitory computer-readable storage medium. Those instructions may then be read and executed by one or more processors to enable the performance of the operations described herein. The instructions may be in any suitable form, such as but not limited to source code, compiled code, interpreted code, executable code, static code, dynamic code, and the like. Such a computer-readable medium may include any tangible non-transitory medium for storing information in a form readable by one or more computers, such as but not limited to read only memory (ROM); random access memory (RAM); magnetic disk storage media; optical storage media; a flash memory, etc.

The term "machine-readable medium" may include any medium that is capable of storing, encoding, or carrying instructions for execution by the machine 700 and that cause the machine 700 to perform any one or more of the techniques of the present disclosure, or that is capable of storing, encoding, or carrying data structures used by or associated with such instructions. Non-limiting machine-readable medium examples may include solid-state memories and optical and magnetic media. In an example, a massed machine-readable medium includes a machine-readable medium with a plurality of particles having resting mass. Specific examples of massed machine-readable media may include non-volatile memory, such as semiconductor memory devices (e.g., electrically programmable read-only memory (EPROM), or electrically erasable programmable read-only memory (EEPROM)) and flash memory devices; magnetic disks, such as internal hard disks and removable disks; magneto-optical disks; and CD-ROM and DVD-ROM disks.

The instructions 724 may further be transmitted or received over a communications network 726 using a transmission medium via the network interface device/transceiver 720 utilizing any one of a number of transfer protocols (e.g., frame relay, internet protocol (IP), transmission control protocol (TCP), user datagram protocol (UDP), hypertext transfer protocol (HTTP), etc.). Example communications networks may include a local area network (LAN), a wide area network (WAN), a packet data network (e.g., the Internet), mobile telephone networks (e.g., cellular networks), plain old telephone (POTS) networks, wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, and peer-to-peer (P2P) networks, among others. In an example, the network interface device/transceiver 720 may include one or more physical jacks (e.g., Ethernet, coaxial, or phone jacks) or one or more antennas to connect to the communications network 726. In an example, the network interface device/transceiver 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 700 and includes digital or analog communications signals or other intangible media to facilitate communication of such software.

The operations and processes described and shown above may be carried out or performed in any suitable order as desired in various implementations. Additionally, in certain implementations, at least a portion of the operations may be carried out in parallel. Furthermore, in certain implementations, less than or more than the operations described may be performed.

The word "exemplary" is used herein to mean "serving as an example, instance, or illustration." Any embodiment described herein as "exemplary" is not necessarily to be construed as preferred or advantageous over other embodiments. The terms "computing device." "user device," "communication station," "station," "handheld device," "mobile device," "wireless device" and "user equipment" (UE) as used herein refers to a wireless communication device such as a cellular telephone, a smartphone, a tablet, a netbook, a wireless terminal, a laptop computer, a femtocell, a high data rate (HDR) subscriber station, an access point, a printer, a point of sale device, an access terminal, or other personal communication system (PCS) device. The device may be either mobile or stationary.

As used within this document, the term "communicate" is intended to include transmitting, or receiving, or both transmitting and receiving. This may be particularly useful in claims when describing the organization of data that is being transmitted by one device and received by another, but only the functionality of one of those devices is required to infringe the claim. Similarly, the bidirectional exchange of data between two devices (both devices transmit and receive during the exchange) may be described as "communicating." when only the functionality of one of those devices is being claimed. The term "communicating" as used herein with respect to a wireless communication signal includes transmitting the wireless communication signal and/or receiving the wireless communication signal. For example, a wireless communication unit, which is capable of communicating a wireless communication signal, may include a wireless transmitter to transmit the wireless communication signal to at least one other wireless communication unit, and/or a wireless communication receiver to receive the wireless communication signal from at least one other wireless communication unit.

As used herein, unless otherwise specified, the use of the ordinal adjectives "first," "second." "third," etc., to describe a common object, merely indicates that different instances of like objects are being referred to and are not intended to imply that the objects so described must be in a given sequence, either temporally, spatially, in ranking, or in any other manner.

Some embodiments may be used in conjunction with various devices and systems, for example, a personal computer (PC), a desktop computer, a mobile computer, a laptop computer, a notebook computer, a tablet computer, a server computer, a handheld computer, a handheld device, a personal digital assistant (PDA) device, a handheld PDA device, an on-board device, an off-board device, a hybrid device, a vehicular device, a non-vehicular device, a mobile or portable device, a consumer device, a non-mobile or non-portable device, a wireless communication station, a wireless communication device, a wireless access point (AP), a wired or wireless router, a wired or wireless modem, a video device, an audio device, an audio-video (A/V) device, a wired or wireless network, a wireless area network, a wireless video area network (WVAN), a local area network (LAN), a wireless LAN (WLAN), a personal area network (PAN), a wireless PAN (WPAN), and the like.

Some embodiments may be used in conjunction with one way and/or two-way radio communication systems, biomedical sensors, wearable devices or sensors, cellular radio-telephone communication systems, a mobile phone, a cellular telephone, a wireless telephone, a personal communication system (PCS) device, a PDA device which incorporates a wireless communication device, a mobile or portable global positioning system (GPS) device, a device which incorporates a GPS receiver or transceiver or chip, a device which incorporates an RFID element or chip, a multiple input multiple output (MIMO) transceiver or device, a single input multiple output (SIMO) transceiver or device, a multiple input single output (MISO) transceiver or device, a device having one or more internal antennas and/or external antennas, digital video broadcast (DVB) devices or systems, multi-standard radio devices or systems, a wired or wireless handheld device, e.g., a smartphone, a wireless application protocol (WAP) device, or the like.

Some embodiments may be used in conjunction with one or more types of wireless communication signals and/or systems following one or more wireless communication protocols, for example, radio frequency (RF), infrared (IR), frequency-division multiplexing (FDM), orthogonal FDM (OFDM), time-division multiplexing (TDM), time-division multiple access (TDMA), extended TDMA (E-TDMA), general packet radio service (GPRS), extended GPRS, code-division multiple access (CDMA), wideband CDMA (WCDMA), CDMA 2000, single-carrier CDMA, multi-carrier CDMA, multi-carrier modulation (MDM), discrete multi-tone (DMT), Bluetooth®, Bluetooth Low Energy, global positioning system (GPS), Wi-Fi, Wi-Max, ZigBee, ultra-wideband (UWB), global system for mobile communications (GSM), 2G, 2.5G, 3G, 3.5G, 4G, fifth generation (5G) mobile networks, 3GPP, long term evolution (LTE), LTE advanced, enhanced data rates for GSM Evolution (EDGE), or the like. Other embodiments may be used in various other devices, systems, and/or networks.

It is understood that the above descriptions are for purposes of illustration and are not meant to be limiting.

Although specific embodiments of the disclosure have been described, one of ordinary skill in the art will recognize that numerous other modifications and alternative embodiments are within the scope of the disclosure. For example, any of the functionality and/or processing capabilities described with respect to a particular device or component may be performed by any other device or component. Further, while various illustrative implementations and architectures have been described in accordance with embodiments of the disclosure, one of ordinary skill in the art will appreciate that numerous other modifications to the illustrative implementations and architectures described herein are also within the scope of this disclosure.

Program module(s), applications, or the like disclosed herein may include one or more software components including, for example, software objects, methods, data structures, or the like. Each such software component may include computer-executable instructions that, responsive to execution, cause at least a portion of the functionality described herein (e.g., one or more operations of the illustrative methods described herein) to be performed.

A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform.

Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, or a report writing language. In one or more example embodiments, a software component comprising instructions in one of the foregoing examples of programming languages may be executed directly by an operating system or other software component without having to be first transformed into another form.

A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

Software components may invoke or be invoked by other software components through any of a wide variety of mechanisms. Invoked or invoking software components may comprise other custom-developed application software, operating system functionality (e.g., device drivers, data storage (e.g., file management) routines, other common routines and services, etc.), or third-party software components (e.g., middleware, encryption, or other security software, database management software, file transfer or other network communication software, mathematical or statistical software, image processing software, and format translation software).

Software components associated with a particular solution or system may reside and be executed on a single platform or may be distributed across multiple platforms. The multiple platforms may be associated with more than one hardware vendor, underlying chip technology, or operating system. Furthermore, software components associated with a particular solution or system may be initially written in one or more programming languages, but may invoke software components written in another programming language.

Computer-executable program instructions may be loaded onto a special-purpose computer or other particular machine, a processor, or other programmable data processing apparatus to produce a particular machine, such that execution of the instructions on the computer, processor, or other programmable data processing apparatus causes one or more functions or operations specified in any applicable flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or operations specified in any flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium which may be used to store the information and which may be accessed. Combinations of any of the above are also included within the scope of CRSM. Alternatively, computer-readable communication media (CRCM) may include computer-readable instructions, program module(s), or other data transmitted within a data signal, such as a carrier wave, or other transmission. However, as used herein, CRSM does not include CRCM.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

What is claimed is:

1. A system, comprising:
   an audio input device;
   a pillow comprising a plurality of regions, wherein a respective region comprises:
      one or more sensors;
      one or more inflatable air bladders; and
      one or more feedback devices;
   a base unit device physically connected to the pillow, wherein the base unit comprises:
      a sound-dampening housing;
      a pump within the sound-dampening housing that is connected to a manifold that independently controls inflation of the one or more inflatable air bladders; and
   electronic circuitry communicatively coupled to the pillow, the electronic circuitry comprising memory storing executable instructions that, as a result of execution by one or more processors, cause the electronic circuitry to:
      obtain, from the audio input device, audio data emitted from a user of the pillow during sleep while the one or more inflatable air bladders are in a first configuration;
      obtaining, from the one or more sensors, sensor data indicating a position or change in the position of the user;
      use a machine-learning model to determine, based on audio data collected by the audio input device and the sensor data collected by the one or more sensors, that the user has experienced an adverse sleep-related condition;
      determine one or more external actions that mitigate the adverse sleep-related condition, wherein the one or more external actions comprise applying, in an alternating fashion, a first lateral force in a first direction at a first time and then applying a second lateral force in a second direction at a second time to create a rocking motion; and
      cause the pillow to apply the one or more external actions on the user.

2. The system of claim 1, wherein the electronic circuitry causes the pillow to use the one or more feedback devices to apply a haptic stimulation.

3. The system of claim 1, wherein the pillow comprises a well for cradling a user's head and an inflatable air bladder in the well for tipping the user's head forward or backward.

4. The system of claim 3, wherein the electronic circuitry causes the pillow to inflate the inflatable air bladder in the well to an angle that opens a user's airway.

5. The system of claim 1, wherein the one or more external actions comprises applying heating or cooling to the user.

6. The system of claim 1, wherein the one or more external actions are applied as micro-motions, macro-motions, haptic stimulation, or a combination thereof.

7. A method for mitigating an adverse sleep-related condition, comprising:
   obtaining multi-modal sensor data of a user that is sleeping;
   providing the multi-modal sensor data to a machine-learning model trained to detect adverse sleep-related conditions;
   determining, based on the multi-modal sensor data provided to the machine-learning model, that the user has experienced the adverse sleep-related condition;
   determining, based on the multi-modal sensor data, one or more external actions to apply to one or more regions of a plurality of regions of a pillow to mitigate the adverse sleep-related condition, wherein the one or more external actions comprises applying, in an alternating fashion, a first lateral force in a first direction at a first time and then applying a second lateral force in a second direction at a second time to create a rocking motion; and
   causing the one or more external actions to be applied to the user at one or more of the plurality of regions of the pillow.

8. The method of claim 7, further comprising:
   determining, based on a sensor located underneath a well of the pillow for receiving a user's head, a first pressure;
   determining a second pressure to mitigate the adverse sleep-related condition; and
   wherein the one or more external actions include inflating an air bladder in the well to apply the second pressure.

9. The method of claim 8, wherein applying the second pressure tilts the user's head and opens a user's airway.

10. The method of claim 7, wherein the one or more external actions cause the user to turn in a direction.

11. The method of claim 7, wherein the one or more external actions comprise applying heating or cooling to the user.

12. The method of claim 7, wherein the one or more external actions are applied as micro-motions, macro-motions, haptic stimulation, or a combination thereof.

13. A system, comprising:
    an insulated housing;
    a motor; and
    electronic circuitry attachable to a pillow, the electronic circuitry comprising memory storing executable instructions that, as a result of execution by one or more processors, cause the electronic circuitry to:
       obtain multi-modal sensor data from an environment in which a user is sleeping on the pillow, the pillow comprising a plurality of regions, wherein a respective region comprising:
          one or more sensors;
          one or more inflatable air bladders; and
          one or more feedback devices;
       determine, based on the multi-modal sensor data, that the user has experienced an adverse sleep-related condition;
       determine, based on the multi-modal sensor data, environment information that is correlated with the adverse sleep-related condition;
       determine one or more external actions that mitigate the adverse sleep-related condition, wherein the one or more external actions comprise applying, in an alternating fashion, a first lateral force in a first direction at a first time and then applying a second lateral force in a second direction at a second time to create a rocking motion; and
       cause the pillow to apply the one or more external actions to the user.

14. The system of claim 13, wherein the electronic circuitry causes the pillow to use the one or more feedback device devices to apply a haptic stimulation.

15. The system of claim 13, wherein the electronic circuitry causes the pillow to inflate the one or more inflatable air bladders.

16. The system of claim 13, wherein the pillow comprises a well for cradling a user's head and an inflatable air bladder in the well for tipping the user's head forward or backward.

17. The system of claim 13, wherein the adverse sleep-related condition is obstructive sleep apnea (OSA).

18. The system of claim 13, wherein the one or more external actions are applied as micro-motions, macro-motions, haptic stimulation, or a combination thereof.

19. The system of claim 13, wherein the one or more external actions comprise a first force applied to a first region and a second force applied to a second region.

* * * * *